US00PP26802P3

(12) United States Plant Patent

Rodriguez Alcazar et al.

(10) Patent No.: US PP26,802 P3

(45) Date of Patent: Jun. 7, 2016

(54) STRAWBERRY PLANT NAMED 'DRISSTRAWFORTYTWO'

(50) Latin Name: *Fragaria×ananassa*
Varietal Denomination: DrisStrawFortyTwo

(71) Applicant: DRISCOLL STRAWBERRY ASSOCIATES, INC., Watsonville, CA (US)

(72) Inventors: Jorge Rodriguez Alcazar, Texcoco (MX); Raquel Cervantes Moreno, Zamora (MX)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 87 days.

(21) Appl. No.: 14/121,765

(22) Filed: Oct. 15, 2014

(65) Prior Publication Data

US 2016/0113176 P1 Apr. 21, 2016

(51) Int. Cl.
*A01H 5/08* (2006.01)

(52) U.S. Cl.
USPC ..... Plt./209

(58) Field of Classification Search
USPC ..... Plt./209
See application file for complete search history.

*Primary Examiner* — Annette Para

(74) *Attorney, Agent, or Firm* — Jondle & Associates, P.C.

(57) ABSTRACT

A new and distinct variety of strawberry plant named 'DrisStrawFortyTwo' particularly characterized by dark red fruit, a mid-season harvest maturity and moderate resistance to *Tetranychus urticae, Botrytis* fruit rot and *Xanthomonas fragariae,* is disclosed.

2 Drawing Sheets

Genus and species: *Fragaria×ananassa.*
Variety denomination: 'DrisStrawFortyTwo'.

BACKGROUND OF THE NEW PLANT

The present invention relates to a new and distinct strawberry variety designated 'DrisStrawFortyTwo' and botanically known as *Fragaria×ananassa.* This new strawberry variety was discovered in Zamora, Mexico in January 2009 and originated from a cross between the proprietary female parent '57N261' (unpatented) and the proprietary male parent '73N203' (unpatented). A single plant was selected and asexually propagated via tissue culture and vegetative cuttings in Shasta County, California in 2009.

'DrisStrawFortyTwo' underwent further testing in Zamora, Mexico for five years (2010-2014). The present invention has been found to retain its distinctive characteristics through successive asexual propagations via stolons and tissue culture.

Plant Breeder's Rights for this variety have not been applied for. 'DrisStrawFortyTwo' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Zamora, Mexico.

1. Dark red fruit;
2. Mid-season harvest maturity; and
3. Moderately resistant to *Tetranychus urticae, Botrytis* fruit rot and *Xanthomonas fragariae.*

DESCRIPTION OF THE PHOTOGRAPHS

The accompanying color photographs show typical specimens of the new variety at various stages of development. The colors shown are as true as can be reasonably obtained by conventional photographic procedures. The photographs were taken from three-month-old plants.

DESCRIPTION OF THE NEW VARIETY

Figure 1:
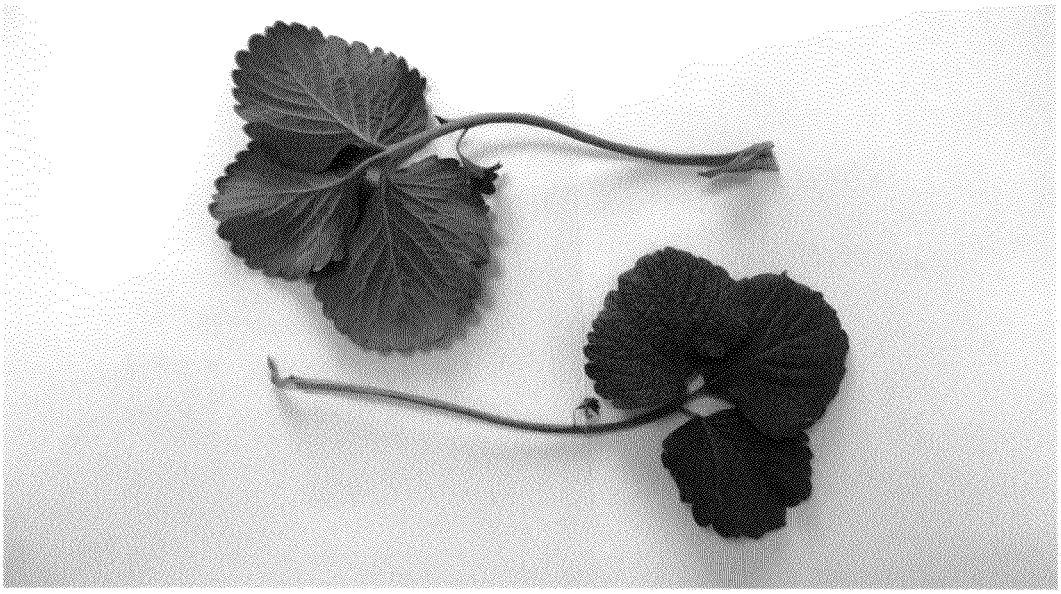
FIG. 1 shows upper and lower surfaces of the leaves of the plant with three leaflets.
Figure 2:
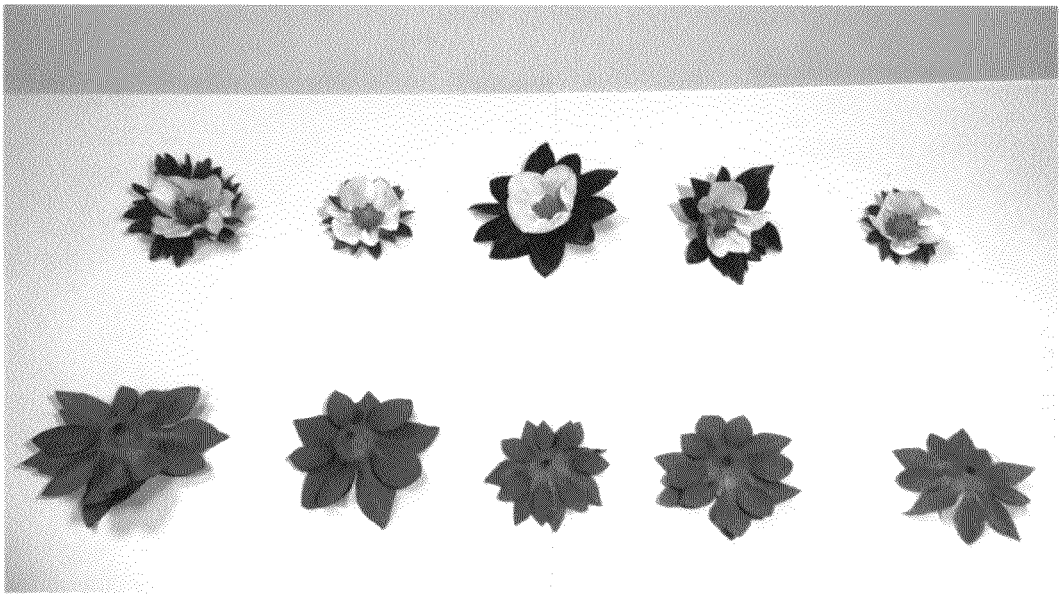
FIG. 2 shows both upper and lower surfaces of the flowers.
Figure 3:
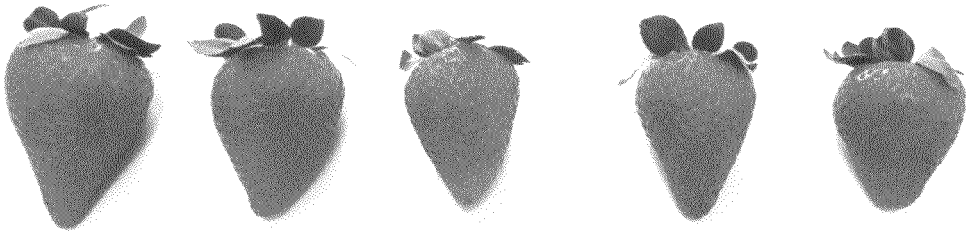
FIG. 3 shows the whole fruit.
Figure 4:
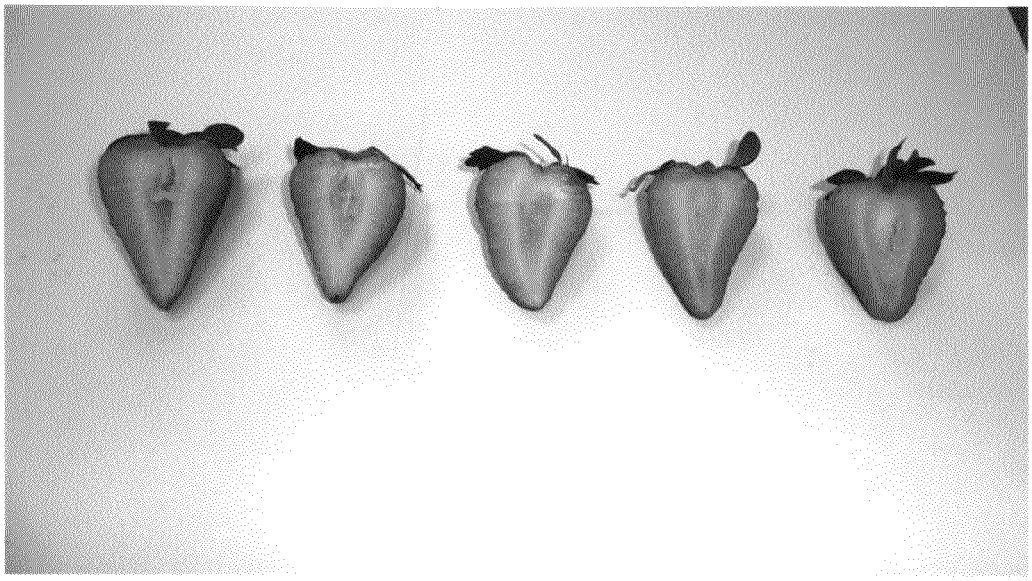
FIG. 4 shows the fruit in longitudinal cross-section.

The following detailed descriptions set forth the distinctive characteristics of 'DrisStrawFortyTwo'. The data which define these characteristics is based on observations taken in Zamora, Mexico from 2010 to 2014. This description is in accordance with UPOV terminology. Color designations, color descriptions, and other phenotypical descriptions may deviate from the stated values and descriptions depending upon variation in environmental, seasonal, climatic, and cultural conditions. 'DrisStrawFortyTwo' has not been observed under all possible environmental conditions. The botanical description of 'DrisStrawFortyTwo' was taken from three-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—*'DrisStrawFortyTwo'.*

Parentage:
*Female parent.*—The proprietary variety '57N261' (unpatented).
*Male parent.*—The proprietary variety '73N203' (unpatented).
Plant:
*Height.*—20.2 cm.
*Diameter.*—27.9 cm.
*Number of crowns/plant.*—4.
*Habit.*—Flat globose.
*Density of individual plant.*—Medium.
*Vigor* (*health and hardiness of plant*).—Medium.
Terminal leaflets:
*Size.*—Medium. Length: 5.7 cm. Width: 5.9 cm. Length/width ratio: 1.0 (As long as broad).
*Number of teeth/terminal leaflet.*—17.
*Shape of teeth.*—Obtuse — serrate to crenate.
*Color.*—Upper surface: RHS 139A (Dark green). Lower surface: RHS 137C (Dark green).
*Shape in cross section.*—Slightly convex.
*Blistering.*—Medium.
*Glossiness.*—Medium.
*Number of leaflets.*—Three only.
*Shape.*—Orbicular.
*Base shape.*—Rounded.
*Apex descriptor.*—Rounded.
*Margin.*—Crenate.
*Margin profile.*—Cupped.
*Variegation.*—Absent.
Petiole:
*Length.*—Medium; 11.7 cm.
*Diameter.*—2.74 mm.
*Pubescence.*—Medium.
*Pose of hairs.*—Upwards.
*Color.*—RHS 144A (Medium yellow-green).
*Bract frequency.*—2.
Petiolule:
*Length.*—8.20 mm.
*Diameter.*—1.72 mm.
*Color.*—RHS 144B (Medium yellow-green).
Stipule:
*Length.*—4.0 cm.
*Width.*—11.90 mm.
*Pubescence.*—Medium.
*Stipule anthocyanin coloration.*—Weak; RHS 52C (Light red).
Stolons:
*Number of stolons.*—Medium.
*Average number of daughter plants per square foot.*—11.
*Anthocyanin coloration.*—Strong; RHS 38C Light red.
*Diameter at bract.*—2.68 mm.
*Thickness.*—Medium.
*Density of pubescence.*—Medium.
Inflorescence:
*Position relative to foliage.*—Above.
*Number of flowers.*—Medium.
*Time of flowering* (*50% of plants at first flower*).—Medium.
*Flowering interval.*—October-February.
*Flower size.*—Medium.
*Diameter.*—26.20 mm.
*Number of flowers per plant.*—9.70.
*Petals.*—Shape: Orbicular. Apex: Rounded. Base: Concavo-convex. Margin: Entire. Spacing: Overlapping. Length: 13.00 mm. Width: 14.10 mm. Length/width ratio: 0.9 (As long as broad). Petal number per flower: 6. Color (upper surface): RHS 155C (White).
*Calyx.*—Diameter: 4.59 mm. Diameter relative to corolla: Much larger. Inner calyx diameter relative to outer: Same size. Insertion of calyx: In a basin — inserted. Pose of calyx segments: Spreading — outwards. Size of calyx in relation to fruit: Slightly larger. Adherence of calyx: Strong.
*Sepal.*—Shape: Elliptical. Apex: Convex. Margin: Entire. Length: 16.80 mm. Width: 8.40 mm. Sepal number: 12.
*Receptacle color.*—RHS 1B (Medium green-yellow).
*Stamen.*—Present. Anther color: RHS 15A (Medium yellow-orange).
*Pedicel.*—Attitude of hairs: Outwards — horizontal.
Fruiting truss:
*Length.*—Medium; 19.2 cm.
*Diameter at base of truss.*—11.15 mm.
*Number of berries per fruiting truss.*—15.
*Attitude at first picking.*—Semi-erect.
*Color at base of truss.*—RHS N144D (Light yellow-green).
Fruit:
*Relative fruit size.*—Medium.
*Length.*—39.90 mm.
*Width.*—29.70 mm.
*Length/width ratio.*—1.3 (Longer than broad).
*Fruit hollow length.*—21.30 mm.
*Fruit hollow width.*—7.30 mm.
*Fruit hollow length/width ratio.*—2.9 (Much longer than broad).
*Fruit hollow center* (*cavity*).—Medium.
*Fruit weight.*—16.6 g.
*Predominant fruit shape.*—Conical.
*Difference in shape between primary and secondary fruits.*—None or very slight.
*Evenness of fruit surface.*—Even or very slightly uneven.
*Fruit skin color.*—RHS 45A (Dark red).
*Evenness of fruit color.*—Even or very slightly uneven.
*Fruit glossiness.*—Strong.
*Achenes.*—Insertion of achenes: Level with surface. Coloration (sunward side of berry): RHS 176C (Medium greyed-orange). Coloration (shaded side of berry): RHS 153C (Medium yellow-green). Number per berry: 459.5. Weight (weight of achenes divided by total # seed): 0.00047660 g. Width of band without achenes: Absent or very narrow.
*Firmness of flesh* (*when fully ripe*).—Firm.
*Color of flesh* (*excluding core*).—RHS 44B (Medium red).
*Color of core.*—RHS 44D (Light red).
*Evenness of flesh color.*—Slightly uneven.
*Distribution of flesh color.*—Marginal and central.
*Sweetness.*—Strong.
*Acidity.*—Weak.
*Texture when tasted.*—Medium.
*Type of bearing.*—Not everbearing — not remontant.
*Harvest interval.*—November-February.
*Harvest maturity.*—Mid-season.
*Production.*—292.2 grams per plant.
Disease and pest resistance:
*Tetranychus urticae.*—Moderately resistant.
*Botrytis fruit rot.*—Moderately resistant.

*Powdery mildew.*—Moderately susceptible.
*Xanthomonas fragariae.*—Moderately resistant.
*Lygus herperus* (*Lygus bug*).—Moderately resistant.

COMPARISON WITH PARENTAL AND COMMERCIAL VARIETIES

When 'DrisStrawFortyTwo' is compared to the female parent '57N261' (unpatented), 'DrisStrawFortyTwo' has better flavor, later production and is a denser plant with more powdery mildew tolerance and more red mite tolerance than '57N261'.

When 'DrisStrawFortyTwo' is compared to the male parent '73N203' (unpatented), 'DrisStrawFortyTwo' has better flavor, is a denser plant with more crowns and is more susceptible to powdery mildew and more tolerant to red mite than '73N203'.

When 'DrisStrawFortyTwo' is compared to the commercial variety 'Driscoll Camarillo' (U.S. Plant Pat. No. 14,771), 'DrisStrawFortyTwo' has a medium dense plant with a flat globose habit, whereas 'Driscoll Camarillo' has a open plant with a globose habit. Additionally, 'DrisStrawFortyTwo' has conical shaped fruit with achenes inserted level with the surface, whereas 'Driscoll Camarillo' has cordate shaped fruit with achenes inserted below the surface.

When 'DrisStrawFortyTwo' is compared to the commercial variety 'Driscoll Osceola' (U.S. Plant Pat. No. 15,752), 'DrisStrawFortyTwo' has conical shaped fruit that has strong sweetness, whereas 'Driscoll Osceola' has cordate shaped fruit that has medium sweetness. Additionally, 'DrisStrawFortyTwo' has fruit with weak acidity and a medium texture when tasted, whereas 'Driscoll Osceola' has fruit with medium acidity and a fine texture when tasted.

We claim:

1. A new and distinct variety of strawberry plant named 'DrisStrawFortyTwo', substantially as illustrated and described herein.

* * * * *